United States Patent
Schena et al.

(10) Patent No.: US 7,815,618 B2
(45) Date of Patent: Oct. 19, 2010

(54) COLOSTOMY BAG CLEANING SYSTEM (76) Inventors: Kenneth R. Schena, 2313 Harrier Run, Naples, FL (US) 34105; Blaine M. Schena, 1717 Icamelia Ave., Naples, FL (US) 34105

( * ) Notice: Subject to any disclaimer, the term of this patent is extended or adjusted under 35 U.S.C. 154(b) by 0 days.

(21) Appl. No.: 12/480,365

(22) Filed: Jun. 8, 2009

(65) Prior Publication Data

US 2009/0247971 A1    Oct. 1, 2009

Related U.S. Application Data

(63) Continuation of application No. 11/328,599, filed on Jan. 11, 2006, now abandoned.

(51) Int. Cl.
A61F 5/44    (2006.01)

(52) U.S. Cl. .................. 604/337; 604/332; 604/333; 604/334; 604/338; 604/339; 604/340; 604/341; 604/343; 604/345; 604/346; 604/347; 604/348; 604/350; 604/351

(58) Field of Classification Search .............. 604/334, 604/332–333, 337, 338–339, 340–348, 350–351
See application file for complete search history.

(56) References Cited

U.S. PATENT DOCUMENTS

| | | | |
|---|---|---|---|
| 2,438,073 A | 3/1948 | Saur | |
| 3,902,496 A | 9/1975 | Eakin | |
| 4,134,404 A | 1/1979 | Williams, Jr. | |
| 4,194,506 A | 3/1980 | Voorhies | |
| 4,654,037 A | 3/1987 | Fenton | |
| 4,778,446 A | 10/1988 | Jensen | |
| 4,911,699 A * | 3/1990 | Fenton | 604/333 |
| 5,096,503 A | 3/1992 | Wellman | |
| 5,454,389 A | 10/1995 | Hubbard et al. | |
| 5,503,633 A * | 4/1996 | Saunders et al. | 604/332 |
| 5,690,621 A * | 11/1997 | Canela | 604/333 |
| 5,738,668 A | 4/1998 | Bugajski | |
| 6,224,581 B1 | 5/2001 | Withers et al. | |

(Continued)

FOREIGN PATENT DOCUMENTS

WO    WO 2004/049984    6/2004

(Continued)

OTHER PUBLICATIONS

Definitions of "sump", "cylindrical", "cylinder", "right circular cylinder", Merriam-Webster OnLine.

Primary Examiner—Tatyana Zalukaeva
Assistant Examiner—Ginger T Chapman
(74) Attorney, Agent, or Firm—Maier & Maier, PLLC (57) ABSTRACT

A closed drainage system for irrigating colostomy bags wherein the bag is irrigated and cleaned while in its operable position associated with the person. More specifically, the invention mounts a manifold within the colostomy bag with an access to a water pressure from outside, the manifold providing a spray dispersion of fluid, or water preferably, at the top of the bag and gravity then drips it down through the bag and out the open bottom, preferably with the residue of the bag being washed out by the water and passing into a toilet where the user flushes the bag to completion of cleaning with all residue from the bag passing into the toilet. A water source from the toilet itself, or other suitable water supply, provides the pressured water to the manifold inside the top of the colostomy bag.

15 Claims, 7 Drawing Sheets

U.S. PATENT DOCUMENTS

| | | |
|---|---|---|
| 6,408,861 B1 | 6/2002 | Ortega |
| 6,532,971 B2 | 3/2003 | Deecki |
| 6,685,684 B1 | 2/2004 | Falconer |
| 6,918,898 B2 | 7/2005 | King |
| 7,160,274 B2 * | 1/2007 | Ciok et al. .................. 604/332 |
| 2003/0139271 A1 | 7/2003 | Nielsen et al. |
| 2003/0220621 A1 | 11/2003 | Arkinstall |
| 2003/0229324 A1 | 12/2003 | King |
| 2004/0054339 A1 | 3/2004 | Ciok et al. |
| 2005/0075616 A1 * | 4/2005 | Holter ....................... 604/332 |
| 2005/0283126 A1 | 12/2005 | Schena et al. |

FOREIGN PATENT DOCUMENTS

| | | |
|---|---|---|
| WO | WO 2005/063152 | 7/2005 |

* cited by examiner

COLOSTOMY BAG CLEANING SYSTEM

RELATED PATENT APPLICATIONS

The present invention is a continuation application of U.S. patent application Ser. No. 11/328,599, filed Jan. 11, 2006, which is a continuation-in-part application of U.S. patent application Ser. No. 10/874,294 filed Jun. 21, 2004, the disclosures of which are incorporated by reference herein in their entireties.

BACKGROUND OF THE INVENTION

A colostomy is a surgical procedure in which the colon or a portion thereof is removed and the digestive tract is attached to an opening created in the abdominal wall, thereby, allowing digested waste to pass through the abdomen. Typically, the waste is then collected by an impervious bag that is secured over the opening. The opening that results from a colonectomy is known as an "ostomy" or a "stoma," and the impervious bag that collects the digestive waste is known as a colostomy bag.

An individual who has had a colostomy must typically remove and empty the colostomy bag several times a day, and must irrigate the ostomy at least every other day to maintain good health and sanitation. An ostomy is irrigated by applying flowing water into the ostomy and then allowing the water to drain.

Figure 1:
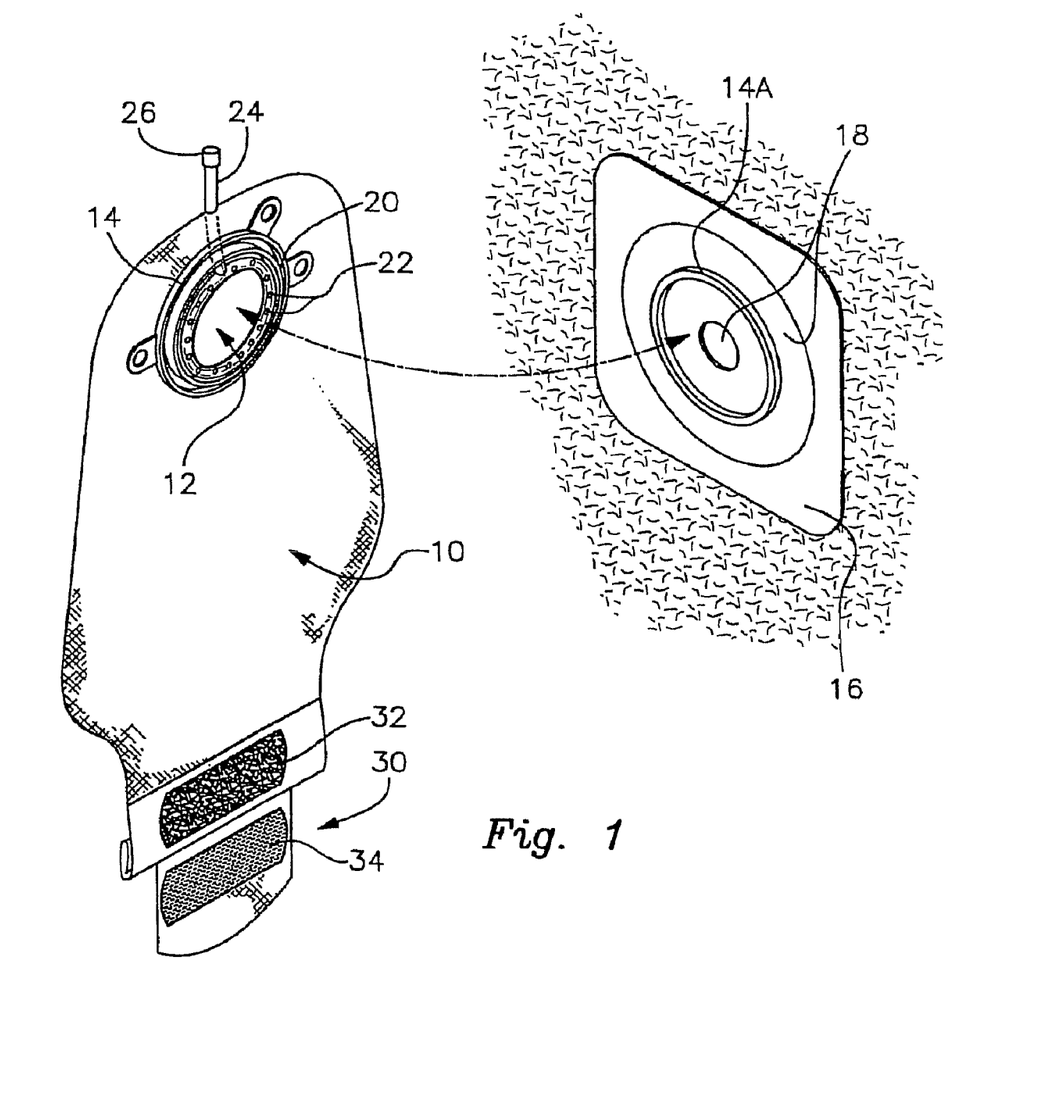
FIG. 1 is a perspective view of the colostomy bag utilizing a manifold around the flanged opening on the bag itself, which then attaches to the flanged fitting positioned on the body of the person, and snaps together to form a fluid-tight seal between the bag and the person.

Examples of ostomy irrigating devices in the prior art or cleansing systems are provided by US Patent Application Publication No. US2003/0229324, which features a closed drainage system that eliminates the necessity to stand over a toilet, as it has its own collection system, but it is a difficult system to use and almost requires the person to be lying down as illustrated in FIG. 1 for any satisfactory use. U.S. Pat. No. 6,408,861 illustrates a urine bag cleaning manifold, which is a very complicated system associated with a shower in a bathtub, and again, is difficult to operate and very elaborate in design. U.S. Pat. No. 5,454,389 teaches an ostomy bag cleaning device that incorporates a mechanism for introducing water into a colostomy bag and then evacuate the waste material into a storage chamber. This device is cumbersome to use and does not provide for a simple cleaning of the colostomy bag without removal from the person.

U.S. Pat. Nos. 5,096,503 and 4,194,506 both teach the general concept of insertion rods being inserted from the bottom of the colostomy bag up into the bag itself, and in both of these systems it's awkward to have to insert a rod up through the bottom of the colostomy bag with whatever drippings and materials that would be coming out, and this is not a satisfactory technique for cleaning the colostomy bag while having the bag still maintained on the person. A similar patent is U.S. Pat. No. 5,738,668, which again inserts a probe up into the bag for cleaning, and again the same problems are inherent. U.S. Pat. No. 6,532,971 teaches a sanitary pouch washer that is designed for simultaneously cleaning the inside and outside of the colostomy bag and is a complicated mechanism and, again, is done with the colostomy bag removed from the person. U.S. Pat. No. 6,224,581 teaches a colostomy bag cleaning appliance having a mounting plate and, again, this is a cleaning method with the bag removed from the person and creates significant complications in achieving the cleaning in a simple and effective manner.

SUMMARY OF THE INVENTION

The present invention is a closed draining system for irrigating ostomies and cleaning colostomy bags utilizing a manifold physically located near the top of the bag that provides a stream of water in a sprayed fashion into the top of the bag for internally cleaning the bag and simultaneously cleaning the ostomy, and with the amount of water added being controlled by the user, the bag still being in place on the person, and the flow from the bag coming out the bottom with the normal opening type bags available today.

Accordingly, it is a principal object of the invention to facilitate cleaning of the colostomy bag and simultaneously irrigating the ostomy by providing a manifold near the top of the colostomy bag that is connected to a source of water under some pressure that can then controllably sprinkle water into the colostomy bag for cleaning and irrigation of the bag and the ostomy, with the flow then directed out the bottom of the normal opening-type colostomy bags. The person still has the colostomy bag attached to their body, and the cleaning takes place preferably in association with drainage into a toilet or other suitable drainage facility.

A further object of the invention is to provide that the cleaning of the colostomy bag takes place with the bag still attached to the body of the person, and it can be done quickly and very effectively on a regular basis during the day.

It is a further object of the invention to provide the manifold in conjunction with a standard colostomy bag flange, which is a flanged ring with adhesive backing that is typically secured to the abdomen of a person with an ostomy. The flange allows a colostomy bag to be easily attached and detached. The colostomy bag attaches to the flanged ring much like a plastic lid attaches to a plastic or metal can, i.e., the colostomy bag and flange snap together to form an airtight seal. Consequently, an irrigating system that uses the same flanged ring is also easily attached and detached and, further, does not necessitate the removal of the bag from the person for the irrigation.

Finally, it is an object of the invention to provide improved elements and arrangements thereof for the purposes described, which is inexpensive, dependable and fully effective in accomplishing its intended purposes.

These and other objects of the present invention will become readily apparent upon further review of the following specifications and drawings.

DESCRIPTION OF THE INVENTION

Referring now to FIG. 1 of the drawings, the numeral 10 indicates a colostomy bag, which has an opening 12 that is surrounded by a plastic ring 14 and attached in a fluid-tight fashion to the bag 10 by suitable means, such as adhesively or by other suitable known means. The ring 14 is formed with a flange that is designed to mate with a similarly formed ring and flange 14A on the person mounted colostomy bag attachment patch 16. The patch 16 is attached by pressure-sensitive adhesive on the back of the patch itself and the respective ring flanges 14 and 14A when snapped together form a fluid-tight seal between the ostomy 18 and the interior of the colostomy bag 10.

The irrigating and cleansing technique of the invention is provided by a circular manifold, generally indicated by numeral 20, which is preferably a soft plastic and encircles the interior of the opening 12 into the colostomy bag 10. A plurality of small holes 22 around the perimeter of the manifold 20 are provided to allow the passage of spray in multiple and random directions of water pressure introduced through an access tube 24 that is connected to a water source not shown via fitting 26.

The colostomy bag 10 in the usual fashion is designed to be opened at the bottom end, generally identified by numeral 30, and effectively, this is a rolled up sealing procedure utilizing hook and loop tape indicated by the loop material 32 and the hook material 34. It is well understood that when this is folded up and the hook and loop attachment is in place the bag is sealed at the bottom, but for the purposes of the irrigation and cleansing of the instant invention, the bag is opened and positioned over the toilet so that irrigation cleansing water passing through the manifold 20 and orifices 22 will flow down through the bag and out the bottom opening 30 and into the toilet, as is shown in more detail in FIG. 2 of the drawings.

Figure 2:
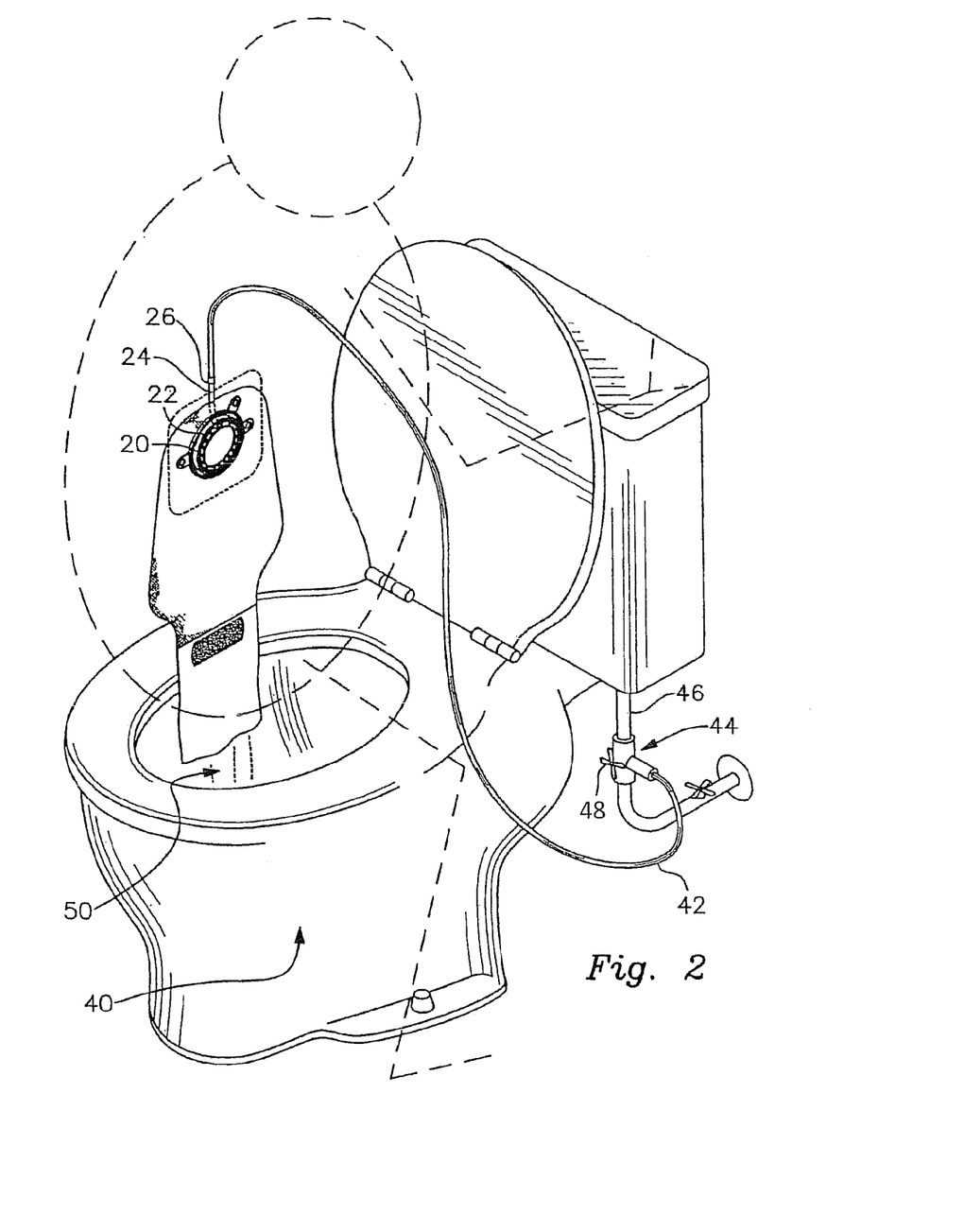
FIG. 2 is a perspective illustration showing a stick figure utilizing the invention by irrigating and flushing the colostomy bag by controlling a valve from the water supply to the toilet with the bottom of the colostomy bag open and flow taking place from the manifold through the bag and into the toilet.

Referring now to FIG. 2, this illustrates a normal toilet indicated generally by numeral 40, and the individual normally sits backward on the toilet seat to operate the invention. A flexible water hose 42 is connected to the fitting 26 to provide water pressure through the conduit 24 and to the manifold 20 for spray out the orifices 22. The water source is by a fitting indicated generally by numeral 44 that fits into the normal water supply tubing to the toilet, indicated by numeral 46, and has the ability to control the amount of flow by a valve, indicated by numeral 48, associated with the conduit 42.

Thus, with reference to FIG. 2, it can be understood that the individual sits backward on the toilet seat, connects the conduit 42 to fitting 26 and then, by adjustively controlling the valve 48, provides a sufficient amount of water pressure into the manifold to cause a flow to irrigate the ostomy 18 as seen in FIG. 1, and to provide a cleansing and irrigating action within the colostomy bag 10, with the residue dripping out at the bottom into the toilet as shown generally by numeral 50.

Figure 3:
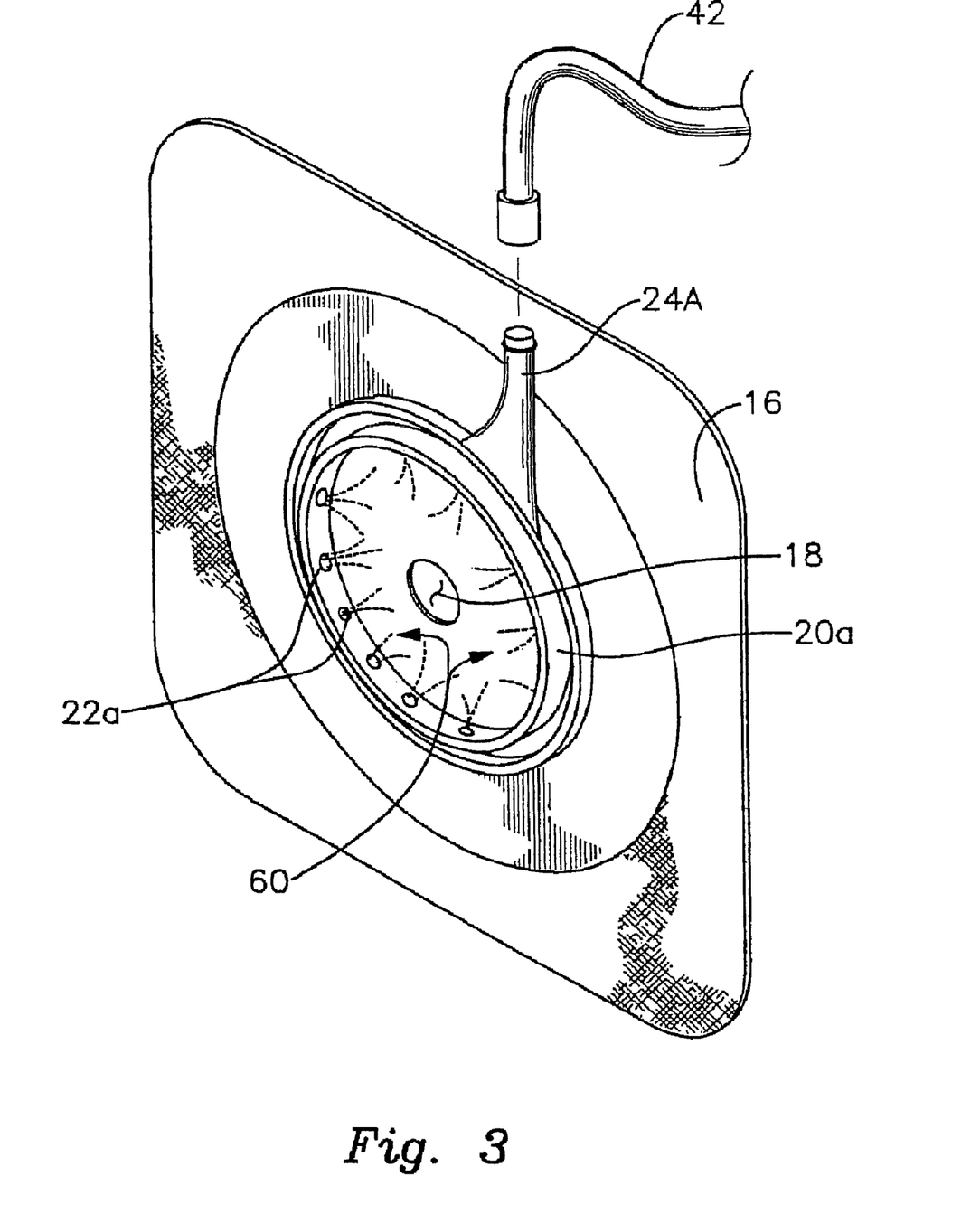
FIG. 3 is a perspective illustration of the manifold associated with the flanged ring and adhesive backing attached to the person and engaging in the snapped fluid-tight relationship with the fitting on the colostomy bag, but wherein the manifold is associated with the fitting carried by the person and functions to clean and irrigate by water pressure coming in sprayed fashion from this manifold.

Referring now to FIG. 3 of the drawing, this shows the embodiment where the manifold, identified generally as numeral 20A, is associated with the RING 14A of the patch 16 that is attached to the skin of the person over the ostomy opening 18, and in this instance, includes an access fitting 24A adaptively connected to the water line 42 so that regulated water pressure provides the spray through orifices 22A illustrated generally by the numeral 60.

Figure 4:
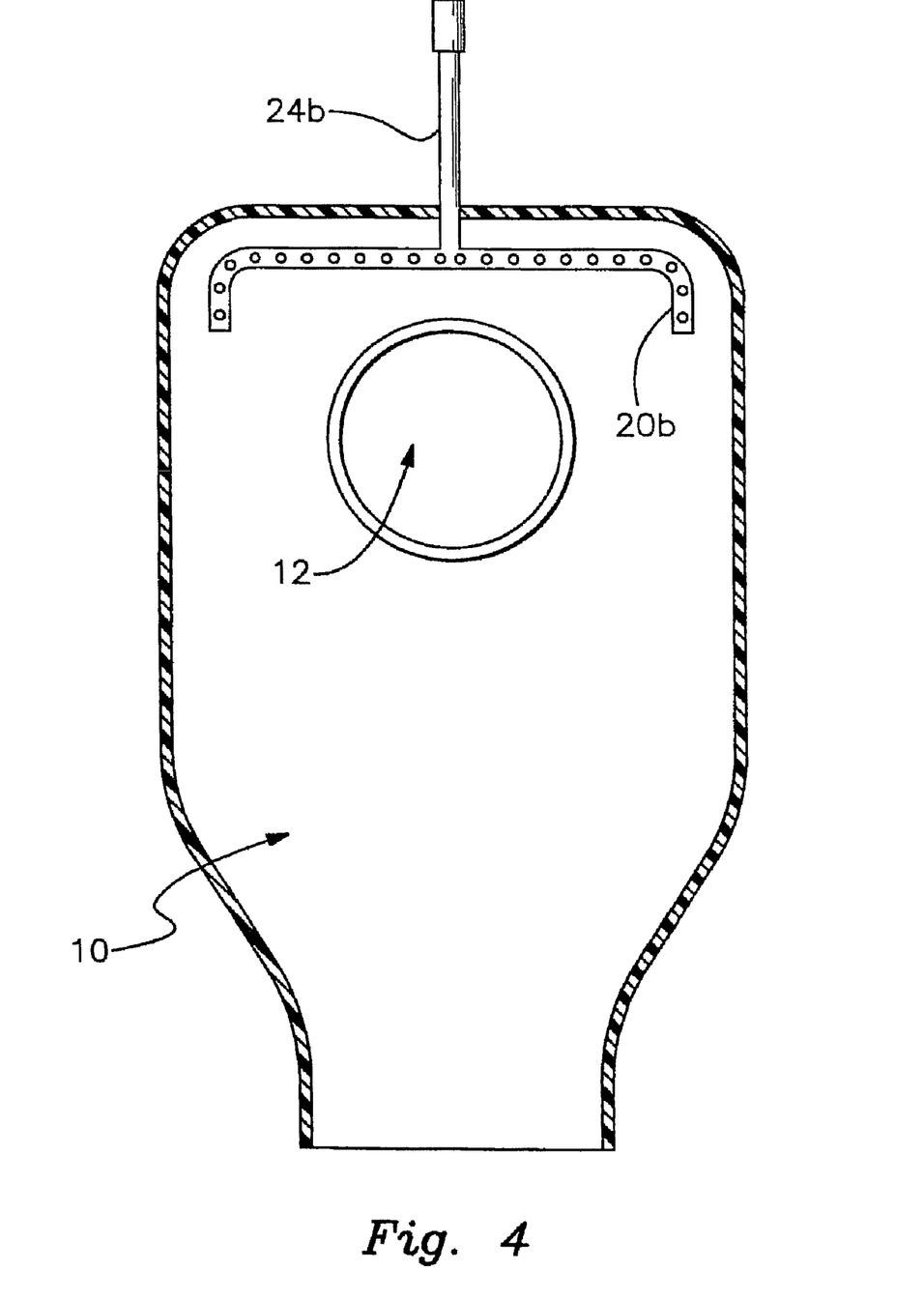
FIG. 4 illustrates a colostomy bag with the manifold positioned around the top of the formed snap connection for the bag itself and water inlet being provided to the manifold around the top of the bag connection opening.

Referring now to FIG. 4, this shows a further embodiment of the invention where the manifold, indicated generally by numeral 20b, as can be seen is positioned above the opening 12 in the colostomy bag 10. A similar water inlet 24b is utilized in this embodiment.

Figure 5:
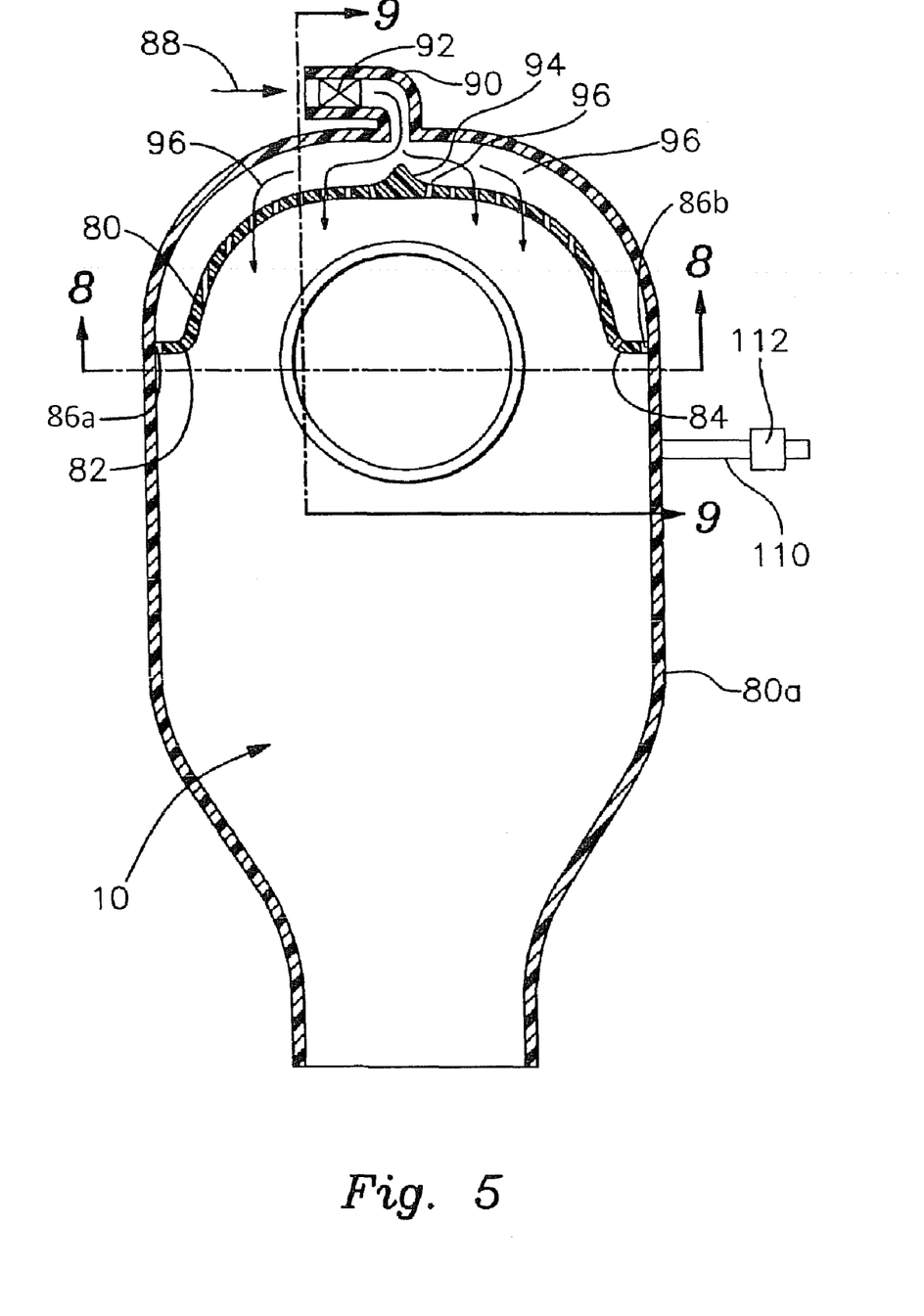
FIG. 5 is a cross-sectional illustration of a modified colostomy bag, having a manifold heat-seal formed into the material itself and at the very top access opening into the bag well above the stoma opening.

Reference should be made to FIG. 5, which is a further modification of the manifold 20b as shown in FIG. 4. More particularly, the manifold in FIG. 5 is formed by heat-sealing the bag 10 along the line shown generally by numeral 80, and this extends from the edge of the bag as shown on the left side at 82 and around below the bottom of the top of the bag and over to the right side, indicated by numeral 84. The sealed line 80 effectively mirrors the shape of the top edge of the bag to form a uniform up-and-down width to the manifold formed by line 80. The plurality of openings 86 are provided then through the heat-sealed portion 80, and this then provides for the random and multi-directed flow of water sprayed as it comes into the access opening indicated by arrow 88 going down into the manifold form by heat-sealed line 80. Access opening into the bag is indicated generally by numeral 90 and, preferably, it includes a one-way valve 92 that prevents backflow up through the opening 90 in case the bag is squeezed or actuated through the force of fluid back up through the opening 90 in the bag. One other feature which is important in this heat-sealed construction is that there is a divider indicated generally by numeral 94 that is part of the heat-formed portion of the manifold and this acts to direct the water flow entering through opening 90 in equal and opposite directions around to the right and the left sides of the bag as is indicated by the water flow arrows indicated generally by numeral 96.

Thus, it should be understood in the embodiment of FIG. 5 that the water flows in the direction indicated by arrow 88 through the one-way valve 92 and into the manifold formed by the heat-sealed line 80 and is directed equally right and left by the divider 94 and then flows through the multiple openings 86 formed by the heat-sealed areas indicated generally then the water flow by numeral 96. The openings 86 provide then for a plurality of openings from the manifold through the heat-sealed portion 80 and facilitate a very significant pattern of water in random directions from the very top of the colostomy bag down over the stoma opening and then as it drains out through the bottom as described with respect to the bag above. Also note the openings 86a and 86b immediately adjacent the outer edge of the bag that send a water spray down the inside edges of the bag for better cleaning of these surfaces Thus, it is seen in FIG. 5 and as also shown in the cross-sectional configurations of FIGS. 8 and 9 that the manifold 20b of FIG. 4 is in fact enhanced and enlarged and modified by the heat-sealed line 80 at the top of the bag in FIG. 5, and the random directed openings 86. It should be understood that the bag 10 is formed from two similarly shaped essentially flat pieces of polymer material that are heat sealed at the periphery in a heat-sealed line 80a as seen in FIGS. 5 and 8.

Figure 9:
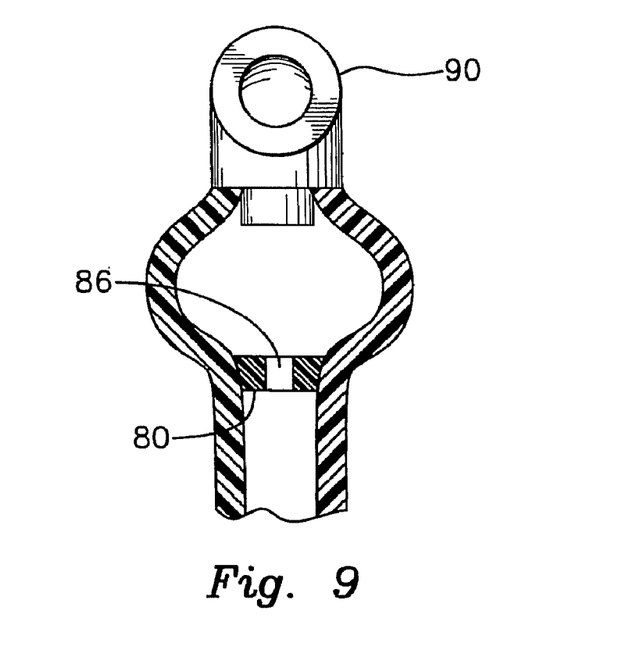
FIG. 9 is a broken-away cross-sectional view of the bag of FIG. 5 taken on line 9-9 of FIG. 5.

FIG. 9 illustrates the cross-sectional portion of the bag of FIG. 5 taken on line 9-9 and it is depicted in the mode where there is water pressure within the manifold opening to form effectively an outwardly formed tubular configuration in the manifold itself as it is pressurized by the water entering in the direction of arrow 88 as shown in FIG. 5.

Figure 8:
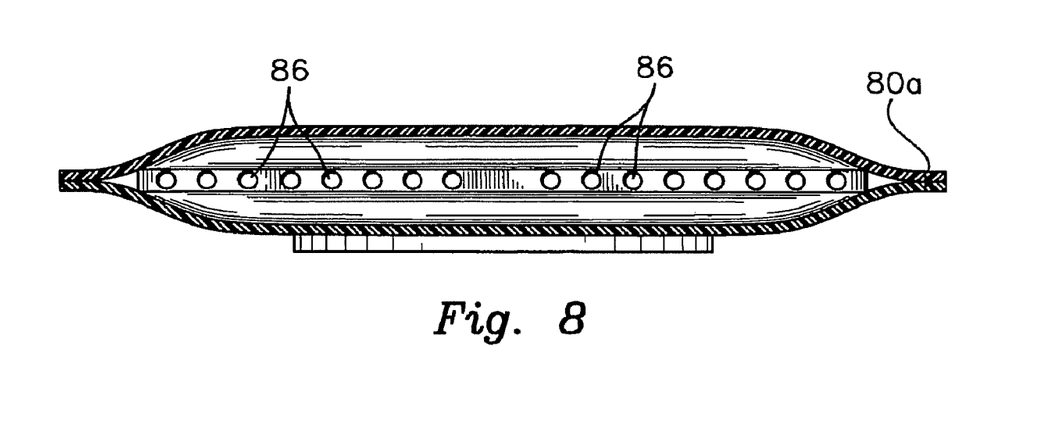
FIG. 8 is a cross-sectional illustration of the bag of FIG. 5 taken on line 8-8 of FIG. 5.

FIG. 8 is simply showing the multiple openings 86 that are formed by the heat-seal across the manifold-forming heat-seal line 80, as shown in FIG. 5.

Figure 6:
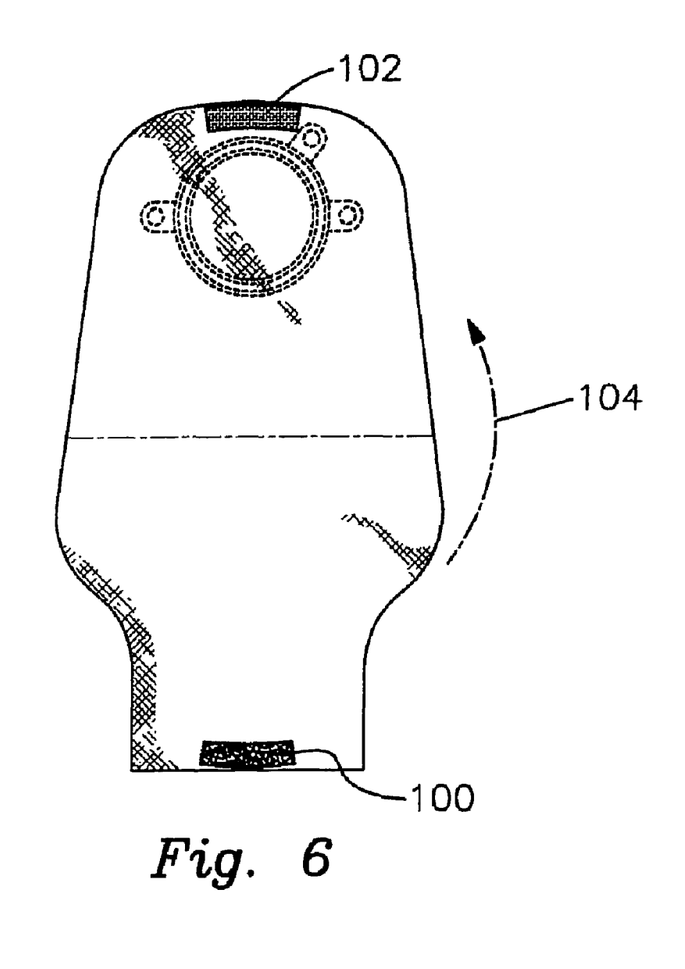
FIG. 6 is a top-plan view of a colostomy bag showing some hook and loop strips along the bag, to be folded up in half and held in that position.
Figure 7:
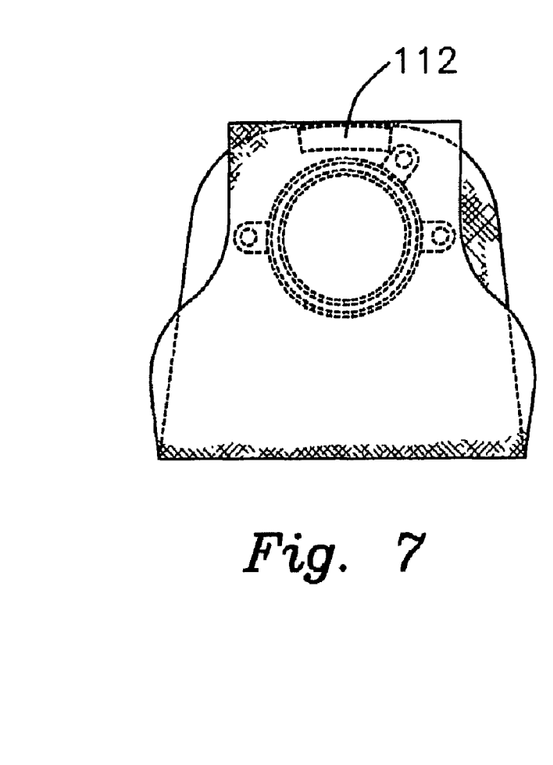
FIG. 7 is the bag shown in FIG. 6 folded-up, reduced in half its length in the position where the beg is held in the folded position by the hook and loop strips.

FIGS. 6 and 7 show hook and loop attachments 100 and 102, which allow the total bag to be folded into the position from FIG. 6 as indicated by the arrow 104 to the half-position shown in FIG. 7. This is convenient in certain times when the bag is not really full to allow a person to have a smaller bag than the full length bag of FIG. 6, and it greatly facilitates keeping the bag from interrupting sleeping because of the smaller size.

Thus, it should be understood that the bag depicted in FIGS. 5, 8 and 9 is a very simply made bag with the heat-seal line 80 being formed in the bag according to standard heat-seal procedures and simultaneously forming the openings 86 so that there will be a random and plentiful flow, much like a shower, from the openings and the water pressure being applied through the opening 90 into the top of the manifold formed by the heat-sealed line 80.

Thus, it should be fully understood that FIGS. 5, 8 and 9 show the heat-sealed pouch configuration consisting of two chambers separated by a heat-sealed septum, line 80, containing a number of communication ports 86 connecting the two chambers. This is the essence of the showing of FIG. 5, with the upper chamber (or plenum) being the smaller of the two, with the means of being connected to an external water supply, and the lower chamber being the larger of the two, with the means of opening the bottom to accommodate the removal of its contents. The communication ports 86 connecting the two chambers are strategically positioned to distribute the water that enters through the smaller, or upper, chamber in a manner that thoroughly cleanses the complete interior of the larger (or lower) chamber. It will also thoroughly cleanse around the stoma opening at the same time.

The heat seal of the tube to the film material and the outer perimeter and septum geometry are done using RF (Radio Frequency or dielectric) sealing methods. Impulse sealing can be used for the outer perimeter and septum seals, but RF is the method of choice when tubing is being sealed to a film material. The actual sealing takes place by locating the layers of the film material onto a fixture that is called a receiver. The sealing die, which is machined to the exact dimensions of the seal design, is then lowered onto the top face of the film layers under a required pressure, and the RF is actuated, which generates an instant heat at the interface of the upper and lower film materials. This creates the optimum seal available for the type of application, and is how line 80 is formed.

The ports 86 are created by machining slots through the heat sealing die in the defined locations. Because the heat sealing process requires two flat surfaces pushing together under a pressure to create the seal, these slots create interruptions in the flat surface, and therefore are not pushing the material together at those locations. Because the material does not have intimate contact at those points, it will not seal together, therefore creating the holes through the septum.

The present design has 18 passages and they are 0.090 wide when the material is lying in the flat position. When the water distribution chamber (or plenum) is filled with the pressurized water, the passages then change their geometry to a rounder hole with a diameter that approaches 0.06 diameter. Their actual shape is probably more oblong, but the effective opening is that of a round hole with that cross section. The ideal size would vary between 0.05 to 0.12 inches diameter. The total number of openings 86 could also vary from about 14 to 24.

It is further important to stress that the system is pressurized by water pressure coming from a water line that normally provides water to the toilet itself or something similar thereto. Another important point included in the modifications shown in FIG. 5 is that there is an external port 110 from the plenum to vent accumulated gas to a charcoal filter 112, thus allowing gas relief without odor.

It should be understood that while FIG. 2 illustrates the water pressure as coming from a water line 46 that normally provides water to the toilet itself, the invention contemplates that any suitable source of water and some pressure will meet the objects of the invention. For example, a bottle of water with the ability to squeeze the bottle will provide pressure. Similarly, a small battery-operated pump with a water source would provide the pressure. It is believed that the invention will best be set up for a person to utilize in their own bathroom in their own home. However, there may be instances when they are traveling or not provided with a facility set up with the ability to hook the water hose to the adaptor 26 and feed the conduit 24 into the manifold, and thus any pressure source will be suitable.

It is also to be understood that the spray holes 22 in the manifold in FIG. 1 are of no particular consequence except to provide a suitable, fairly fine, spray that will tend to both wash and clean and irrigate the residue inside the colostomy bag itself so as to facilitate cleaning in the shortest possible time. It has been found that this system can provide cleaning in just a few minutes and can be done several times a day very conveniently by virtue of the very simple application of water pressure through the manifold to clean the colostomy bag itself.

It is to be understood that the ease and the functioning of this invention is the fact that the manifold is positioned high in the colostomy bag, thus, with a large spray pattern clears the bag from the top down, and it has been found it is desirable to have the manifold positioned no lower than the opening 12 in the colostomy bag for the stoma for attachment to the stoma flange 14A. This then provides for good gravity flow of the water being used in the irrigating and cleansing system, allowing it to flow down through the bag, picking up all residue and out the bottom opening 30. It also should be understood that any colostomy bag that opens at the bottom end will work with the invention.

It is to be understood that the scope of the invention is not to be limited by the descriptions and explanations set forth above, but that the invention encompasses any and all embodiments within the scope of the following claims.

What is claimed is:

1. A cleansing system for a colostomy bag comprising,
    a flexible colostomy bag having a fluid supply opening formed at a proximal longitudinal end of the colostomy bag, a drain opening formed at a distal longitudinal end of the colostomy bag and substantially axially aligned with the fluid supply opening, and a stoma opening formed between the fluid supply opening and the drain opening;
    a manifold shaped to substantially mirror the proximal longitudinal end of the colostomy bag, coupled with the fluid supply opening and formed between the fluid supply opening and the stoma opening, the manifold having a plurality of openings defined therein and a divider disposed thereon, the divider axially aligned with the fluid supply opening; and a fluid supply source to provide fluid under pressure through the fluid supply opening and into the manifold, wherein the divider directs the fluid under pressure to the plurality of holes in the manifold throughout an upper portion of the colostomy bag and the fluid under pressure flows through the drain opening at the distal end of the colostomy bag; and a port to vent gas through an odor-controlling filter.

2. The cleansing system of claim 1, wherein the fluid under pressure that is directed by the divider in the manifold disperses fluid through the plurality of holes such that the fluid is dispersed from the plurality of holes to clean the substantially entire interior of the colostomy bag.

3. The cleansing system of claim 1, further comprising a one-way valve disposed in the fluid supply opening that prevents reverse flow of fluids.

4. The cleansing system of claim 1, wherein the colostomy bag is formed from two similarly shaped, substantially flat pieces of polymer material that are heat sealed at a periphery in a heat-sealed line.

5. The cleansing system of claim 1, wherein the manifold is formed with a heat sealed line from a proximal latitudinal end of the colostomy bag to a distal latitudinal end of the colostomy bag.

6. The cleansing system of claim 1, wherein the plurality of openings defined in the manifold are formed with heat seals.

7. The cleansing system of claim 1, further comprising a fastener that facilitates folding and securing the colostomy bag in a smaller size.

8. The cleansing system of claim 7, wherein the fastener is a hook and loop fastener.

9. A colostomy bag comprising, a bag having a fluid supply opening formed at a proximal longitudinal end of the bag, a drain opening formed at a distal longitudinal end of the bag and substantially axially aligned with the fluid supply opening, and a stoma opening formed between the fluid supply opening and the drain opening, the stoma opening facilitating coupling the bag to an ostomy; and a manifold shaped to substantially mirror the proximal longitudinal end of the colostomy bag, coupled with the fluid supply opening and formed between the fluid supply opening and the stoma opening, the manifold having a plurality of openings defined therein and divider disposed thereon, the divider axially aligned with the fluid supply opening; and a filtered vent port.

10. The colostomy bag of claim 9, further comprising a one-way valve disposed in the fluid supply opening.

11. The colostomy bag of 9, wherein the colostomy bag is formed from two similarly shaped, substantially flat pieces of polymer material that are heat sealed at a periphery in a heat-sealed line.

12. The colostomy bag of claim 9, wherein the manifold is formed from a proximal latitudinal end of the colostomy bag to a distal latitudinal end of the colostomy bag.

13. The colostomy bag of claim 9, further comprising a fastener that facilitates folding and securing the colostomy bag in a smaller size.

14. The colostomy bag of claim 13, wherein the fastener is a hook and loop fastener.

15. The colostomy bag of claim 9, wherein the vent port has an odor-controlling filter.

* * * * *